United States Patent [19]

Gramlich et al.

[11] Patent Number: 4,758,548
[45] Date of Patent: Jul. 19, 1988

[54] NOVEL ALIPHATIC ALDEHYDES AND THEIR PREPARATION

[75] Inventors: Walter Gramlich, Edingen-Neckarhausen; Hardo Siegel, Speyer, both of Fed. Rep. of Germany

[73] Assignee: BASF Aktiengesellschaft, Rheinland-Pfalz, Fed. Rep. of Germany

[21] Appl. No.: 68,116

[22] Filed: Jun. 30, 1987

[51] Int. Cl.⁴ ............................................. A61K 7/46
[52] U.S. Cl. ..................... 512/27; 512/25; 512/26; 568/448; 568/458
[58] Field of Search ............... 568/458, 461, 664, 448, 568/463; 512/26, 27

[56] References Cited

U.S. PATENT DOCUMENTS

| | | | |
|---|---|---|---|
| 2,852,563 | 9/1958 | Hagemeyer et al. | 568/461 |
| 3,463,818 | 8/1969 | Blumenthal | 568/463 |
| 3,531,510 | 9/1970 | Blumenthal | 260/465.9 |
| 3,706,804 | 12/1972 | Siddall | 568/448 |
| 3,762,423 | 10/1973 | Simpson et al. | 131/17 |
| 3,922,310 | 11/1975 | Dietrich et al. | 568/448 |
| 3,922,351 | 11/1975 | Dietrich et al. | 568/448 |
| 4,239,657 | 12/1980 | Nissen et al. | 568/462 |
| 4,240,985 | 12/1980 | Shepherd, Jr. | 568/458 |
| 4,270,006 | 5/1981 | Heilen et al. | 568/463 |
| 4,525,298 | 6/1985 | Schulte-Elte et al. | 512/25 |

FOREIGN PATENT DOCUMENTS

| | | |
|---|---|---|
| 1149344 | 5/1963 | Fed. Rep. of Germany . |
| 2229269 | 12/1972 | Fed. Rep. of Germany . |
| 2351057 | 4/1974 | Fed. Rep. of Germany . |
| 2723636 | 12/1978 | Fed. Rep. of Germany . |
| 3245047 | 2/1983 | Fed. Rep. of Germany ........ 512/25 |
| 2077344 | 10/1971 | France . |
| 1539310 | 1/1979 | United Kingdom . |

OTHER PUBLICATIONS

Houben–Weyl, Methoden der Org. Chemie, vol. 7/1, pp. 76–85.
P. Rylander, Catalytic Hydrogenation in Organ. Chem., Academic Press, 1979, p. 74f.

Chemical Abstracts, vol. 44, No. 7, Apr. 10, 1950, col. 2911h.

*Primary Examiner*—Werren B. Lone
*Attorney, Agent, or Firm*—Oblon, Fisher, Spivak, McCelland & Maier

[57] ABSTRACT

Aliphatic aldehydes of the general formula I

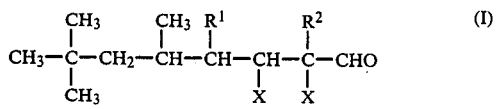

where
$R^1$ is hydrogen or methyl,
$R^2$ is a straight-chain or branched alkyl radical of 1 to 4 carbon atoms and the two radicals X are each hydrogen or together form a further C—C bond, in particular
2,5,7,7-tetramethyloctanal,
2,4,5,7,7-pentamethyloctanal,
2-ethyl-5,7,7-trimethyloctanal and
2,5,7,7-tetramethyl-2-octen-1-al, are used in scent compositions and are prepared by a process in which an aldehyde of the general formula II

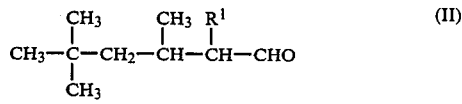

is condensed with an aldehyde of the general formula III

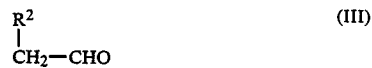

in the presence of an aldol condensation catalyst to give the substituted octenal of the general formula I, and, if required, the latter is partially hydrogenated or reduced to give the ocorresponding octanal of the formula I.

7 Claims, No Drawings

NOVEL ALIPHATIC ALDEHYDES AND THEIR PREPARATION

The present invention relates to aliphatic aldehydes of the general formula I

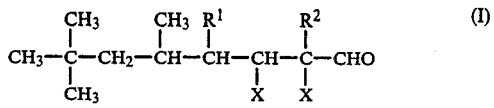

where
R¹ is hydrogen or methyl,
R² is a straight-chain or branched alkyl radical of 1 to 4 carbon atoms, preferably methyl or ethyl, and the two radicals X are each hydrogen or together form a further C—C bond, in particular 2,5,7,7-tetramethyloctanal, 2,4,5,7,7-pentamethyloctanal, 2-ethyl-5,7,7-trimethyloctanal and 2,5,7,7-tetramethyl-2-octen-1-al, their preparation and their use as scents.

Because the availability of many natural scent components is unreliable and generally dependent on many unpredictable factors, and it is necessary to adapt to changing tastes in fashion, the scent industry is constantly in need of novel scents which, either alone or in the form of compositions, constitute useful perfumes having interesting notes. Furthermore, there is a steadily growing trend toward perfuming products in daily use, such as cosmetics, and industrial articles, such as glues, detergents and cleaning agents, products for indoor sprays, etc.

Since little is known about the relationships between structure and factory properties and controlled synthesis of scents with the desired odor is impossible, it is an object of the present invention to provide compounds which have useful fragrance properties, ie. novel fragrance notes, or are capable of replacing scents which are expensive or difficult to obtain, and furthermore can be prepared from readily available intermediates which cause little environmental pollution.

In the search for economical, readily obtainable novel scents having interesting fragrance notes, the novel aliphatic aldehydes of the formula I were found.

Some compounds having a certain structural relationship with the compounds according to the invention are already known.

For example, U.S. Pat. No. 3,531,510 discloses a 5,7,7-trimethyloctenenitrile which has a fragrance resembling that of cloves or iris and having an earthy, fresh, green note.

Furthermore, German Laid-Open Application DOS No. 2,723,636 discloses 2,3,5,5-tetramethylhexanal (aldehyde of TMH), which has a fresh, green fragrance reminiscent of herbs, flowers and ozone.

Commercial 3,5,5-trimethylhexanal has a strong green character with an oily note reminiscent of green vegetables.

Furthermore, German Laid-Open Application DOS No. 3,245,047 discloses compounds of the formula

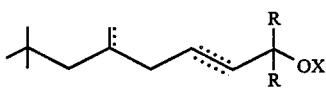

(R = H or alkyl X = H or organic acyl)

of which 5,7,7-trimethyloctyl propionate with its fruity, pear-like note appears particularly interesting.

The novel aliphatic aldehydes of the formula I have useful fragrance properties which differ very substantially from those of the compounds described above. For example, 2,5,7,7-tetramethyloctanal (I; R¹=H, R²=CH₃) has a very interesting, intense lily-of-the-valley note. This is very surprising since Example 5 of the abovementioned German Laid-Open Application DOS 3,245,047 describes the preparation of 6,8,8-trimethyl-2-nonanol by oxidation of 5,7,7-trimethyloctanol to give 5,7,7-trimethyloctanol, followed by Grignard methylation, and the aldehyde which occurs as an intermediate, and which differs from the abovementioned aldehyde of the formula I only in that it lacks a dimethyl group, was quite obviously classified as unimportant from the factory point of view, although the object of this invention was to prepare good scents.

Particularly interesting aldehydes of the formula I are those in which R¹ is hydrogen or methyl, R² is methyl or ethyl and X is hydrogen.

A particularly useful substance among the preferred compounds is 2,5,7,7-tetramethyloctanal, whose intense but fine lily-of-the-valley note is particularly interesting; this unique note cannot be compared with that of any current commercial product.

2,4,5,7,7-Pentamethyloctanal too has an interesting floral fragrance with a sweet flag note.

2-Ethyl-5,7,7-trimethyloctanal also has an interesting floral note and furthermore a very fresh effect.

Because of their interesting fragrance properties, the novel aldehydes of the general formula I can advantageously be used as scents or components of perfume oils for cosmetic or industrial applications. They can be used in a wide range of concentrations in compositions and can readily be combined with conventional perfume ingredients and other scents to give novel compositions. The amount of the novel compounds in scent compositions can be from 1 to 50% by weight, based on the weight of the composition.

Compositions of this type can be used for perfuming cosmetic preparations, such as creams, lotions, scents, toilet soaps, oral hygiene agents and aerosols, and in extract perfumery. They can also be employed for improving the fragrance of industrial products such as cleaning agents, detergents and softeners. Usually, from 0.05 to 2% by weight, based on the total product, of a composition of this type is used.

In addition to the use of the novel aldehydes of the formula I for imparting, improving or modifying the fragrance properties of perfumes or perfumed products, the present invention furthermore relates to a process for the preparation of these aliphatic aldehydes of the formula I wherein an aldehyde of the general formula II

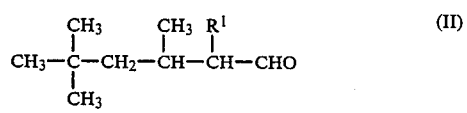

is condensed with an aldehyde of the general formula III

where $R^1$ and $R^2$ have the above meanings, in the presence of an aldol condensation catalyst to give the substituted octenal of the general formula I, and, if required, the latter is partially hydrogenated or reduced to give the corresponding octanal of the formula I.

The aldehydes of the formulae II and III are commercial compounds. In particular, the aldehydes of the formula III, such as propionaldehyde, butyraldehyde, isovaleraldehyde, n-valeraldehyde and n-hexanal, are important industrial intermediates and are therefore available economically in sufficient amounts.

The aldol condensation is carried out in a conventional manner, so that detailed descriptions are unnecessary. It is preferably carried out in the presence of a basic catalyst. In particular, concentrated potassium hydroxide solution or sodium hydroxide solution is used as the basic catalyst. Lower alcohols, such as methanol or ethanol, have proven particularly useful solvents. Regarding further details of aldol condensations, reference may be made to Houben-Weyl, Methoden der Organischen Chemie, volume 7/1, pages 76-85, in particular 76-78.

If $R^1$ is hydrogen, both the aldehydes II and the aldehydes III are unsubstituted in the α-position, with the result that a mixture of three different aldol condensates is formed (a homoaldol condensate of aldehyde II, a homoaldol condensate of aldehyde III and a heteroaldol condensate).

In a preferred version, the basic catalyst is initially taken together with the solvent (eg. methanol), and a mixture of aldehydes II and III is added dropwise at elevated temperatures, preferably from 50° to 60° C.

The molar ratio of the aldehydes can be varied depending on the radicals $R^1$ and $R^2$, although in general an excess of the aldehyde III, which is generally the more reactive one, is used.

In this version, the homoaldol condensation of the aldehyde II can be virtually completely prevented. The homocondensates of the aldehyde of the formula III can readily be isolated and are frequently industrially important intermediates, such as 2-methyl-2-pentenal (from propanal) or the large-scale chemical product 2-ethyl-2-hexenal (from butanal), so that useful products are obtained in addition.

The resulting octenals of the formula I can, if desired, then be hydrogenated or reduced to give the corresponding saturated aldehydes of the formula I by a conventional method. Palladium catalysts on various carriers, such as carbon, alumina, silica gel or bauxite, have proven particularly useful for this selective hydrogenation. Furthermore, lower alcohols are advantageous solvents for this step. For further details of such selective hydrogenation reactions, reference may be made to, for example, P. Rylander, "Catalytic Hydrogenation in Organic Synthesis, Academic Press 1979, page 74 et seq.

Because of the particular fragrance properties described, the novel aldehydes can advantageously be used as scents or components of scent compositions and perfume oils for cosmetic applications. The fact that they can be prepared in a simple manner from readily available starting materials is also important.

EXAMPLE 1

Preparation of 2,5,7,7-tetramethyl-2-octenal 128 g (4 moles) of methanol and 2 g (0.05 mole) of NaOH were initially taken under nitrogen in a reaction flask and were refluxed. A mixture of 142 g (1 mole) of 3,5,5-trimethylhexanal and 116 g (2 moles) of propionaldehyde was added dropwise to this solution in the course of 10 minutes. The resulting reaction mixture was kept at the boil for 1 hour (h) and then brought to pH 4-5 with an 80% strength aqueous acetic acid solution. After washing twice with water, the organic phase was separated off and worked up by fractional distillation. 32 g of unconverted 3,5,5-trimethylhexanal, as light ends, and 113 g of 2,5,7,7-tetramethyl-2-octenal (bp.=108°-111° C./14 mbar) were obtained, corresponding to a selectivity of 81%, based on trimethylhexanal; $n_D^{25}=1.4580$.

IR: 2,956, 16,981, 1,644, 1,246 cm$^{-1}$.

$^1$H-NMR: 0.85 (9H, s), 0.92 (3H, d), 1-1.28 (2H, m), 1.75 (3H, s), 1.8 (1H, m), 2.1-2.35 (2H, m), 6.53 (1H, t), 9.4 (1H, s) δ ppm; MS: M$^+$=182 (3.5); m/e: 111 (6.5), 97 (4.5), 84 (54), 71 (5), 57 (100), 41 (25), 29 (14).

The compound has an interesting sensual note.

EXAMPLE 2

Preparation of 2,5,7,7-tetramethyloctanal

In a hydrogenation autoclave, 250 g (1.37 moles) of 2,5,7,7-tetramethyl-2-octenal, dissolved in 500 ml of methanol, were hydrogenated in the presence of 25 g of a 0.5% strength palladium/alumina catalyst at 80° C., initially under a hydrogen pressure of 25 bar, and after 2-3 h, under 55 bar. The total hydrogenation time was 10 h. The catalyst was filtered off, after which fractional distillation gave 245 g (1.33 moles) of 2,5,7,7-tetramethyloctanal (bp.=68° C./0.3 mbar; $n_D^{25}=1.4308$), corresponding to a yield of 96% of theory. The compound was in the form of a diastereomeric mixture.

IR: 2,956, 1,728, 1,476, 1,465, 1,365 cm$^{-1}$.

$^1$H-NMR: 0.89 (9H, s), 0.92 (3H, d, 1-1.5 (9H, m), 1.7 (1H, m), 2.25 (1H, m), 9.15 (1H, s) δ ppm; MS: m$^+$=184 (0.1); m/e: 151 (2.5), 142 (2.0); 128 (6.0), 126 (5.5), 110 (5.5), 95 (13.5), 81 (5), 71 (22), 57 (100), 41 (32).

The compound has a very interesting fresh intense lily-of-the-valley note.

EXAMPLE 3

2-Ethyl-5,7,7-trimethyloctanal

2-Ethyl-5,7,7-trimethyloctanal was prepared from 3,5,5-trimethylhexanal and n-butanal similarly to Examples 1 and 2; it was obtained in the form of a diastereomeric mixture.

bp.=102° C./14 mbar; $n_D^{25}=1.4339$.

IR: 2,557, 1,728, 1,476, 1,464, 1,365, 1,247 cm$^{-1}$.

$^1$H-NMR: 0.88 (9H, s), 0.89 (3H, d), 0.89 (3H, t), 0.95-1.7 (9H, m), 2.13 (1H, m), 9.63 (1H, s) δ ppm; MS: M$^+$=198 (0.6); m/e: 142 (7), 126 (7.5), 109 (8), 95 (6.8), 83 (5), 72 (37), 57 (100), 41 (27), 29 (18).

The compound has a fresh floral note.

EXAMPLE 4

2,4,5,7,7-Pentamethyloctanal 2,4,5,7,7-Pentamethyloctanal was prepared from 2,3,5,5-tetramethylhexanal (aldehyde of TMH from Dragoco, Holzminden) and propionaldehyde similarly to Examples 1 and 2; the compound was obtained in the form of a diastereomeric mixture.

bp.=54° C./0.2 mbar; $n_D^{25}$=1.4398.

IR: 2,958, 1,727, 1,477, 1,465, 1,393, 1,381, 1,365, 1,113 cm$^{-1}$.

$^1$H-NMR: 0.78–0.9 (6H, m), 0.9 (9H, s), 0.9–1.8 (9H, m), 2.4 (1H, m), 9,58 and 9.63 (1H, s) δ ppm; MS: M+ =198 (0.1); m/e: 140 (3.5), 109 (6.5), 99 (12), 85 (13), 75 (3.5), 71 (17), 57 (17), 43 (47).

The compound has an interesting floral fragrance with a sweet flag note.

Example of use

A basic perfume composition having a floral character was prepared by mixing the following components:

| | |
|---|---|
| Citronellol | 33.7 g |
| Rhodinol P (Rhone-Poulenc) | 11.3 g |
| Hydroxycitronellal (BASF) | 9.6 g |
| Benzyl benzoate | 6.7 g |
| Dimethyl phthalate | 2.25 g |
| Indole 10% | 2.25 g |
| | 95.00 g |
| 2,5,7,7-Tetramethyloctanal | 5.00 g |
| | 100.00 g |

The addition of 2,5,7,7-tetramethyloctanal reinforced the natural floral fresh fragrance of the composition.

We claim:

1. An aliphatic aldehyde of the formula I

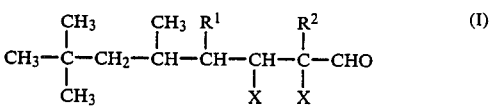

where
R$^1$ is hydrogen or methyl,
R$^2$ is a straight-chain or branched alkyl radical of 1 to 4 carbon atoms and the two radicals X are each hydrogen or together form a further C—C bond.
2. 2,5,7,7-Tetramethyloctanal.
3. 2,4,5,7,7-Pentamethyloctanal.
4. 2-Ethyl-5,7,7-trimethyloctanal.
5. 2,5,7,7-Tetramethyl-2-octen-1-al.
6. A scent composition containing one or more of the aliphatic aldehydes as claimed in claim 1.
7. A scent composition which contains from 1 to 50% by weight of the aliphatic aldehydes of the formula I as claimed in claim 1.

* * * * *